United States Patent [19]
Wiedemann

[11] Patent Number: 6,110,851
[45] Date of Patent: Aug. 29, 2000

[54] PROCESS FOR PRODUCING A CERAMIC MATERIAL BASED ON CALCIUM PHOSPHATE COMPOUNDS AND USE OF THIS MATERIAL

[76] Inventor: Wolfgang Wiedemann, Am Ziegelbaum 51, D-97204, Hochberg, Germany

[21] Appl. No.: 09/155,953

[22] PCT Filed: Mar. 29, 1997

[86] PCT No.: PCT/DE97/00653

§ 371 Date: Dec. 7, 1998

§ 102(e) Date: Dec. 7, 1998

[87] PCT Pub. No.: WO97/37932

PCT Pub. Date: Oct. 16, 1997

[30] Foreign Application Priority Data

Apr. 9, 1996 [DE] Germany ............... 196 14 016

[51] Int. Cl.[7] .................................. C01B 25/32
[52] U.S. Cl. ............... 501/1; 106/35; 501/123; 423/308; 423/309; 423/311; 423/314; 423/315
[58] Field of Search .............. 501/1, 123; 106/35; 423/308, 309, 311, 314, 315

[56] References Cited

U.S. PATENT DOCUMENTS

| 3,012,852 | 12/1961 | Nelson | .................................. 423/309 |
| 3,473,889 | 10/1969 | Shen | ..................................... 423/315 |

FOREIGN PATENT DOCUMENTS

| 36 35 060 A1 | 10/1989 | Germany . |
| 43 02 072 A1 | 1/1993 | Germany . |
| WO 86/01726 | 3/1986 | WIPO . |
| WO 89/05625 | 6/1989 | WIPO . |
| WO 94/02412 | 2/1994 | WIPO . |

*Primary Examiner*—C. Melissa Koslow
*Attorney, Agent, or Firm*—Michael L. Dunn

[57] ABSTRACT

A method of producing a ceramic material based on calcium phosphate compounds for use in dental medicine by adding a phosphate solution to a calcium salt solution, separating the precipitation formed in the reaction solution from the mother liquor, drying, crushing and sintering is characterised in that at least one orthophosphate and at least one diphosphate, each in solution, are added to the calcium salt solution, wherein the molar ratio of diphosphate to orthophosphate is in the region of 0.001 to 0.03:1, and keeps the pH-value of the reaction solution in which the precipitation is formed in the region of 7.5 to 12 until the end of the reaction.

23 Claims, No Drawings

PROCESS FOR PRODUCING A CERAMIC MATERIAL BASED ON CALCIUM PHOSPHATE COMPOUNDS AND USE OF THIS MATERIAL

The invention relates to a method of producing a ceramic material based on calcium phosphate compounds for use in dental medicine.

In dental medicine, plastics materials, such as amalgams, synthetic materials and inorganic cements are usually used for removing defects, particularly carious defects. Another method of repairing carious defects is to use metal, e.g. gold, inlays. There are drawbacks with these conventional materials, such as allergies which may occur with amalgams, insufficient mechanical strength, and the high cost in the case of precious metal inlays.

The production is also already known of plastically deformable ceramic tooth filling materials, dental cements and dental bonding agents, whereof the mechanical and physical-chemical properties resemble those of the natural tooth enamel. These are de-mineralised in acid medium like natural tooth enamel and re-mineralised by saliva, and they bond firmly with the natural tooth enamel.

EP-A-89 900 578.9 relates to a tooth filling material composed of calcium phosphate compounds which have a proportion of pores of 20 to 70% by volume. The essence of this publication consists in utilising the porous tooth filling material in order to enable the ions in the saliva to diffuse into the cavity filled with the porous hydroxylapatite body and to allow solid calcium phosphate to form there which will largely resemble the tooth enamel in terms of its chemical composition and crystalline structure.

DE-A-3 935 060 describes a ceramic material for tooth fillings and -crowns based on calcium phosphate compounds in which the atomic ratio of calcium to phosphorus of the calcium phosphate compounds is in total less than 1.65. These ceramic materials are produced either by grinding a mixture of a calcium phosphate compound of poor solubility with an easily soluble calcium phosphate compound, or by precipitating an aqueous solution of calcium- and phosphate compounds followed by sintering at 800 to 1400° C. Similar materials and methods for use as tooth filling material, dental cement or dental bonding agents are also described in DE-A-4 302 072. However, these known manufacturing methods have considerable drawbacks since even slight deviations in the method parameters, such as reaction time or reaction temperature, can lead to very different reaction products, and the reaction conditions can be considerably impaired in respect of sintering capability and corrosion properties due to these slight deviations. As a result, with the known methods, wherein the pH-value shifts in the reaction solution so that at the end of the reaction it is 7, there cannot be any reproducible product quality, and the methods cannot therefore be carried out successfully on an industrial scale.

The problem which forms the basis of the invention is therefore to obtain a method of producing a ceramic material which can be used in dental medicine and which has properties similar to those of natural tooth enamel, which results in a product quality well able to be reproduced and which therefore can also be used for production on an industrial scale. This problem is solved by way of the method according to claim 1.

This method according to the invention for producing a ceramic material based on calcium phosphate compounds for use in dental medicine by adding a phosphate solution to a calcium salt solution, separating off the precipitate formed in the reaction solution from the mother liquor, drying, crushing and sintering is characterised in that at least one orthophosphate and at least one diphosphate, each in solution, are added to the calcium salt solution, wherein the molar ratio of diphosphate to orthophosphate is in the region of 0.001 to 0.03:1, and keeps the pH-value of the reaction solution in which the precipitation is formed in the region of 7.5 to 12.

With the known methods, when heating up takes place during the sintering operation, a certain amount of diphosphate first of all forms from which tricalcium phosphate occurs when further heated. However, the amount of diphosphate which is formed is greatly dependent upon the exact reaction conditions, and is difficult to reproduce. On the other hand, according to the invention, a specific quantity of diphosphate is added to the reaction solution, which, despite small fluctuations in the reaction conditions, produces product materials which are reproducible in terms of their properties like sintering capability and corrosive behaviour. With use on an industrial scale, waste is therefore reduced to a minimum.

The material can be de-mineralised and re-mineralised like natural tooth enamel, i.e. demineralising in acid medium increases the surface porosity, whilst the effects of saliva or enriched re-mineralising media cause re-mineralisation by the growth or new formation of hydroxyl apatite crystals, wherein the pores close again, and in the cavity which is filled with the ceramic material a filling material occurs which is comparable to the natural hydroxyl apatite. The tooth filling material, and also the surrounding tooth enamel, are thereby firmly anchored to one another, and have the same mechanical and physical-chemical properties.

The ceramic material produced according to the invention contains a crystallite phase of poor solubility composed of calcium phosphates like hydroxyl apatite ($Ca_5[PO_4]_3$ [OH]), fluoro apatite ($Ca_5[PO_4]_3F$) or mixtures thereof, in an easily soluble matrix phase composed of calcium phosphate compounds like tricalcium phosphate, brushite ($CaHPO_4 \cdot 2H_2O$), monetite ($CaHPO_4$), carbonate apatite (see WO 86/01 726), octacalcium phosphate ($Ca_8H_2[PO_4]_6 \cdot 5H_2O$) or mixtures thereof. "Of poor solubility" means solubility in water compared to hydroxyl apatite, whilst "easily soluble" means a relatively high degree of solubility as hydroxyl apatite.

The preferred molar ratio of diphosphate to orthophosphate is in the region of 0.004 to 0.3:1, in particular 0.01 to 0.02:1, so that for each mole of orthophosphate 1 to 2 molar per cent of diphosphate is added.

The pH-value of the reaction solution is adjusted by adding alkali at the start of precipitation, preferably by adding ammonia solution, so that the pH-value stays at 7.5 or above during the reaction. The pH-value of the reaction solution is preferably kept in the region of 8 to 9 during the entire precipitation operation. Purely aqueous solutions are preferably used, although the concept of the invention can, of course, also be realised by adding an organic solvent like ethanol or acetone. This can control the crystallinity of the precipitation product, for example.

The starting compounds used are a calcium salt with an acid residue which is volatile when heated and phosphates with cations which are volatile when heated, wherein calcium salt mixtures, orthophosphate mixtures, diphosphate mixtures or monosubstances can be used. The purpose of the cations and acid residues which are volatile when heated is not to have to purify the product of undesirable cations and anions, or not to have to wash them prior to drying because washing in this way can change the stoichiometry in respect of the ratio of calcium to phosphate and the properties of the product can be undesirably changed thereby. These ions which are volatile when heated can be those which are formed by $CO_2$, nitrogen oxides and $H_2O$ or $NH_3$ when heated, for example. It is expedient and preferable to use calcium nitrate and ammonium phosphate.

Conversion of the calcium salt with orthophosphate and diphosphate, with a specific quantity of the latter, by the tricalcium phosphate content of the sintering body can be controlled accurately in aqueous solution, expediently at a temperature in the region of 45 to 120° C., preferably in the region of 50 to 90° C., in particular in the region of 60 to 80° C. Advantageously, the calcium salt solution which has been heated to the desired reaction temperature e.g. 75° C., is applied, and the aqueous solution of the adjusted mixture of orthophosphate and diphosphate is added slowly with vigorous and thorough mixing. The adding is expediently done drop by drop whilst the reaction solution is stirred in order to distribute the phosphate solution which has been dropped into the calcium salt solution quickly. The precipitation takes place virtually in a moment.

After the reaction and precipitation are concluded, the pH-value should still be at least 7.5. The precipitate in the reaction solution is then separated from the mother liquor, possibly by filtering or centrifuging, and dried, crushed and sintered. During crushing, it is expedient if the particles can reach a size of less than 30 μm, usually of between 0.5 and 20 μm, and, in particular, of between 1 and 10 μm.

Calcium salt and orthophosphate can be converted with each other in the method according to the invention in the stoichiometric molar ratio ±20% required for the formation of hydroxyl apatite. However, it is expedient if the quantities of converted calcium salt and phosphates are adjusted in the reaction solution so that a calcium deficit results and the atomic ratio of calcium to phosphorus in the reaction solution is 1.65 or less, preferably in the region of between 1.3 to 1.65.

Whereas the diphosphate which is added in accordance with the invention serves to produce the desired quantity of tricalcium phosphate in the sintered product, in order to control the growth of crystallite during sintering it can be expedient to add small quantities of polyphosphate, in particular from 0.005 to 1 molar per cent, in relation to the amount of calcium present in the reaction solution. It is also expedient to add fluoride and/or carbonate in the conventional way to the reaction solution, e.g. the former to form fluoro apatite.

Sintering is carried out in the conventional way at 800 to 1400° C., in particular at 900 to 1200° C., preferably at 1100 to 1200° C. The sintering time is expediently 15 minutes to 24 hours.

Before pressing and sintering it can be expedient for the product of precipitation to undergo secondary ageing in raised water vapour, wherein the raised water vapour advantageously has a temperature of 100 to 350° C., and the secondary ageing of the crystallites expediently takes place during a period of 1 hour to 10 days.

It can also be expedient to condense the pulverised precipitation product by explosive compression to form the parent substance for sintering. The explosive condensing of the precipitation product is advantageously carried out isostatically.

In order to produce a plastic material, such as a material for tooth crowns, filling material, dental cement or dental bonding agent, the sintered body can be crushed again. To that end, a synthetic resin substance or a mixing liquid or carrier liquid is added to the pulverised ceramic material.

The invention shall be described in greater detail by way of the following examples.

EXAMPLE 1

48.5 g $Ca(NO_3)_2 \cdot 4H_2O$ is dissolved in 1.7 litres of bidistilled water, and with a solution of ammonia the pH-value is set at 8.6 (measured at 75° C.). At a temperature of 75° C., 300 ml of an aqueous solution which contains 16.25 g diammonium hydrogenorthophosphate and 91 ml of 2N ammonia solution is added slowly drop by drop. The solution contains 1.65 mmol/l ammonium diphosphate. The precipitate formed ages at room temperature and is filtered off after 12 hours. The pH-value of the excess is 8.2 (at room temperature). No Ca can be detected in the excess, and the concentration of phosphate is 6 μmol/l. After drying for 24 hours at 100° C., careful crushing in the mortar, pressing and sintering for 1 hour at 1150° C., an opaque sintered body is obtained which has the required de-mineralising- and re-mineralising properties.

EXAMPLE 2

48.5 g $Ca(NO_3)_2 \cdot 4H_2O$ is dissolved in 1.7 litres of bidistilled water, and with a solution of ammonia the pH-value is set at 8.6 (measured at 75° C.). At a temperature of 75° C., 300 ml of an aqueous solution which contains 16.25 g diammonium hydrogenorthophosphate and 91 ml of 2N ammonia solution and 30 mg ammonium diphosphate is added slowly drop by drop. The solution contains 43 μmol/l phosphorus as polyphosphate. The precipitate ages at room temperature and is filtered off after 12 hours. The pH-value of the excess is 8.2 (at room temperature). 0.6 mmol/l Ca and 3.8 μmol/l phosphate can be detected in the excess. After drying for 24 hours at 100° C., careful crushing in the mortar, pressing and sintering for 1 hour at 1150° C., an opaque sintered body is obtained which has good corrosion properties and re-mineralisation properties.

EXAMPLE 3

48.5 g $Ca(NO_3)_2 \cdot 4H_2O$ is dissolved in 1.7 litres of bidistilled water, and with a solution of ammonia the pH-value is set at 8.6 (measured at 75° C.). At a temperature of 75° C., 300 ml of an aqueous solution containing 16.25 g diammonium hydrogenorthophosphate and 91 ml 2N ammonia solution is added slowly drop by drop. The solution also contains additionally 86 μmol phosphorus as polyphosphate and 0.9 mmol/l ammonium diphosphate. The precipitate ages at room temperature and is filtered off after 12 hours. The pH-value of the excess is 8.2 (at room temperature). 0.7 mmol/l Ca is contained in the excess, and no phosphate can be detected. After drying for 24 hours at 100° C., careful crushing in the mortar, pressing and sintering for 1 hour at 1150° C., an opaque sintered body is obtained which very closely resembles the behaviour of enamel in terms of de-mineralisation and re-mineralisation.

What is claimed is:

1. A method of producing a ceramic material based on calcium phosphate compounds for use in dental medicine, comprising:

adding phosphate solution to a calcium salt solution to form a reaction solution;

maintaining the pH-value of the reaction solution in the region of 7.5 to 12 until precipitation ceases at an end of the reaction;

separating formed precipitate from liquid; and drying, crushing and sintering, wherein at least one orthophosphate and at least one diphosphate, each in solution, are added to the calcium salt solution, wherein the molar ratio of diphosphate to orthophosphate is in the region of 0.001 to 0.03:1.

2. A method according to claim 1, wherein the molar ratio of diphosphate to orthophosphate is kept in the region of 0.004:1 to 0.03:1.

3. A method according to claim 1, wherein the molar ratio of diphosphate to orthophosphate is kept in the region of 0.01:1 to 0.02:1.

4. A method according to claim 1 wherein the pH-value of the reaction solution is kept in the region of 8 to 9 until the end of the reaction.

5. A method according to claim 3 wherein the pH-value of the reaction solution is kept in the region of 8 to 9 until the end of the reaction.

6. A method according to claim 1 wherein temperature of the reaction solution is from 45 to 120° C.

7. A method according to claim 1 wherein temperature of the reaction solution is from 50 to 90° C.

8. A method according to claim 1 wherein temperature of the reaction solution is from 60 to 80° C.

9. A method according to claim 2 wherein temperature of the reaction solution is from 45 to 120°C.

10. A method according to claim 1 wherein drops of the phosphate solution are added to the calcium salt solution, where the calcium solution is at a temperature in the range of 45 to 120° C.

11. A method according to claim 1, wherein the Ca/P atomic ratio in the reaction solution is kept to 1.65 or less.

12. A method according to claim 1, wherein Ca/P atomic ratio in the reaction solution is in the region of 1.3 to 1.65.

13. A method according to claim 1, wherein polyphosphate is additionally added to the reaction solution in a quantity which corresponds to 0.005 to 1 molar per cent of P, in relation to the amount of calcium contained.

14. A method according to claim 1, wherein a compound selected from the group consisting of fluoride, carbonate and mixtures thereof is additionally added to the reaction solution.

15. A method according to claim 1, wherein sintering takes place at a temperature of 800 to 1400° C.

16. A method according to claim 11 wherein sintering takes place at a temperature of 1100 to 1200° C.

17. A method according to claim 1, wherein the calcium salt has an anion which emits a volatile acid when heated.

18. A method according to claim 17, wherein the calcium salt is calcium nitrate.

19. A method according to claim 11, wherein the phosphates have a cation which emits a volatile material when heated.

20. A method according to claim 1, wherein the phosphates used are ammonium phosphates.

21. A method according to claim 1, wherein following drying and crushing and prior to sintering the product of precipitation is condensed explosively.

22. A method according to claim 21, wherein the explosive condensing is carried out isostatically.

23. A method according to claim 1, wherein prior to sintering the product of precipitation undergoes secondary aging in steam under pressure at from 100 to 350° C. for a period of from 1 hour to 10 days.

* * * * *

UNITED STATES PATENT AND TRADEMARK OFFICE
CERTIFICATE OF CORRECTION

PATENT NO. : 6,110,851
DATED : August 29, 2000
INVENTOR(S) : Wolfgnag Weidemann

It is certified that error appears in the above-identified patent and that said Letters Patent is hereby corrected as shown below:

Claim 16,
Please change the dependency from 11 to 1.

Claim 19,
Please change the dependency from 11 to 1.

Signed and Sealed this

Twentieth Day of November, 2001

Attest:

*Nicholas P. Godici*

*Attesting Officer*

NICHOLAS P. GODICI
*Acting Director of the United States Patent and Trademark Office*